United States Patent [19]

Suryanarayanan

[11] Patent Number: 4,991,191
[45] Date of Patent: Feb. 5, 1991

[54] QUANTITATIVE ANALYSIS OF THE ACTIVE TABLE INGREDIENT BY POWER X-RAY DIFFRACTOMETRY

[75] Inventor: Raj G. Suryanarayanan, Minneapolis, Minn.

[73] Assignee: The Regents of the University of Minnesota, Minneapolis, Minn.

[21] Appl. No.: 475,404

[22] Filed: Feb. 5, 1990

[51] Int. Cl.$^5$ .................... G01N 23/207; G01N 31/00
[52] U.S. Cl. ......................... 378/75; 250/304
[58] Field of Search ........................... 250/304; 378/75

[56] References Cited

U.S. PATENT DOCUMENTS 4,592,082  5/1986  Pawloski ........................ 378/75

OTHER PUBLICATIONS

Jenkins, Ron, QXD-A System for Quantitative Powder Diffractometry, 1973, pp. 24–31, Norelco Reporter/vol. 20, No. 2.
Alexander and Klug, Basic Aspects of X-Ray Absorption, in Anal. Chem. 20: pp. 886–889 (1948).
H. P. Klug and L. E. Alexander, X-Ray Diffraction Procedures for Polycrystalline and Amorphous Materials, 2nd ed., Wiley, N.Y. (1974), 531–562.
J. W. Shell, X-Ray and Crystallographic Applications in Pharmaceutical Research II, in J. Pharm. Sci, 52: pp. 24–29 (1963).
R. Suryanarayanan, Pharm. Res 6: pp. 1017–1024 (1989).
C. Lefebvre, A. M. Guyot-Hermann, M. Draguet-Brughmans et al., Drug Dev. Ind. Pharm 12: pp. 1913–1927 (1986).

Primary Examiner—Janice A. Howell
Assistant Examiner—Don Wong
Attorney, Agent, or Firm—Vidas & Arrett

[57] ABSTRACT

A method for quantitatively analyzing solid mixtures of a crystalline ingredient and an excipient component in commercial pharmaceutical tablets by x-ray powder diffractometry using the intact tablet as is, without special sample preparation.

The method comprises the steps of:
  irradiating the table with x-rays in a powder x-ray diffraction device and determining the integrated intensity of diffracted x-rays, I, at an angular range producing at least one x-ray diffraction line characteristic of said crystalline ingredient;
  determining the ratio of said value I to a diffracted x-ray intensity value, $I_o$, obtained on a second compressed tablet consisting of said crystalline ingredient at said angular range; and
  comparing the determined ratio $I/I_o$ to a set of predetermined standard values of said ratio for known mixtures of said crystalline ingredient and said excipient component to quantitate said crystalline ingredient in said first compressed tablet.

10 Claims, 9 Drawing Sheets

Weight fraction of carbamazepine (II)

QUANTITATIVE ANALYSIS OF THE ACTIVE TABLE INGREDIENT BY POWER X-RAY DIFFRACTOMETRY

BACKGROUND OF THE INVENTION

Many pharmaceuticals are dispensed in mass produced tablet forms which are required to fulfil several requirements before being considered acceptable by the United States Pharmacopeia. In order to ensure that the amount of active ingredient in the tablets is within acceptable limits of the labelled amount, the Pharmacopeia requires that the finished dosage form be assayed. Chromatographic and spectrophotometric methods are widely used to assay the active ingredient in tablets. The test for "uniformity of dosage units" is designed to ensure that the variation in the amount of active ingredient between the individual tablets is within acceptable limits.

DESCRIPTION OF PRIOR ART

Quantitative analysis of mixtures of solids by powdered x-ray diffractometry has previously been reported by Alexander and Klug in *Anal. Chem.* 20: 886–889 (1948) and in *X-Ray Diffraction Procedures for Polycrystalline and Amorphus Materials*, 2nd ed. Wiley, N.Y., 1974, pp. 531–562. Other examples in the literature of analysis of inorganic and organic mixtures by quantitative powder x-ray diffractometry exist including J. W. Shell, *J. Pharm. Sci.*, 52: 24–29 (1963).

The prior art has suggested that quantitative x-ray diffractometry can successfully be used in some pharmaceutical systems. However, quantitative analysis has been restricted to powder samples. The direct analysis of finished dosage forms such as tablets has not been attempted. The theoretical basis for quantitative analysis by powder x-ray diffraction assumes that the powder mixture is a uniform randomly oriented mixture. Because packing of crystalline powders can cause the powder particles to develop a preferred orientation, the prior art has previously taught that sample loading must be carefully performed to minimize preferred orientation and assure reliable results. This laborious sample preparation step provides a significant limitation on the use of powder x-ray diffraction analysis in situations, such as quality control situations, where large numbers of samples must be analyzed regularly.

The prior art x-ray diffractometry techniques for quantitative pharmaceutical analyses have also been limited because experimentally observed intensities have not been compared with the calculated (theoretical) intensity values. Therefore it is not known if the systems fulfil all the assumptions based on which the theory of quantitative x-ray diffractometry is developed.

SUMMARY OF THE INVENTION

The present invention pertains to a process for quantitatively analyzing solid mixtures in tablet forms, especially commercial pharmaceutical tablets, by x-ray powder diffractometry. The method allows the use of the intact tablet as is, without special sample preparation. Because of the inventive method, substantial savings in sample preparation time are accomplished. Additionally, x-ray exposure for short periods of time is unlikely to cause decomposition of most solid materials. Consequently for such materials the method is nondestructive and allows the samples to be retained. The traditional quality control procedures (chromatography, spectrophotometry) cause destruction of the dosage unit. Therefore only a representative sample in a given batch can be analyzed. If the situation warrants that each of the dosage units be analyzed, this method would be ideal. Moreover the nondestructive nature of the analysis allows the sample to be retained permitting analyses to be replicated later as necessary.

The invention comprises in one aspect a process for analyzing a known crystalline ingredient in a first compressed tablet consisting essentially of a solid mixture of the crystalline ingredient and an excipient component, the method comprising:

irradiating the tablet with x-rays in a powder x-ray diffraction device and determining an intensity value, I, indicative of the quantity of diffracted x-rays at an angular range producing at least one x-ray diffraction line characteristic of said crystalline ingredient;

determining the ratio of said value I to a diffracted x-ray intensity value, $I_0$, obtained on a second compressed tablet consisting of said crystalline ingredient at said angular range; and comparing the determined ratio $I/I_0$ to a set of predetermined standard values of said ratio for mixtures of said crystalline ingredient and said excipient component to quantitate said crystalline ingredient in said first compressed tablet.

BRIEF DESCRIPTION OF THE FIGURES

FIG. 7 is a plot of the relative intensities of the sum of 8 lines of lithium carbonate as a function of:

$$\frac{1}{x_1(\mu_1^* - \mu_2^*) + \mu_2^*}$$

The line is based on theoretical values while the data points are experimental measurements.

Figure 8:
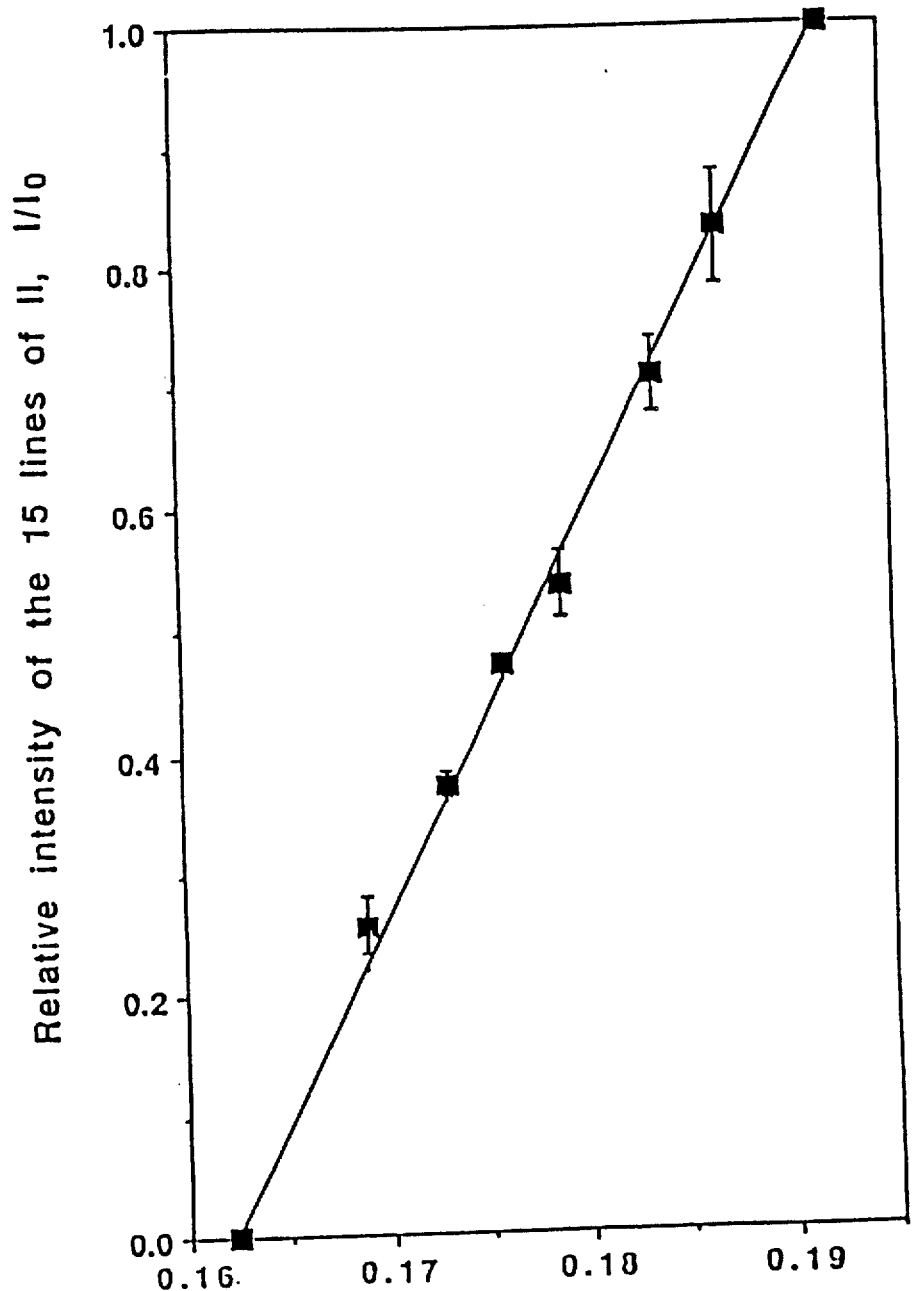

FIG. 8 is a plot of the relative intensities of the sum of 15 lines of carbamazepine as a function of:

$$\frac{1}{x_1(\mu_1^* - \mu_2^*) + \mu_2^*}$$

The line is based on theoretical values while the data points are experimental measurements.

Figure 9:
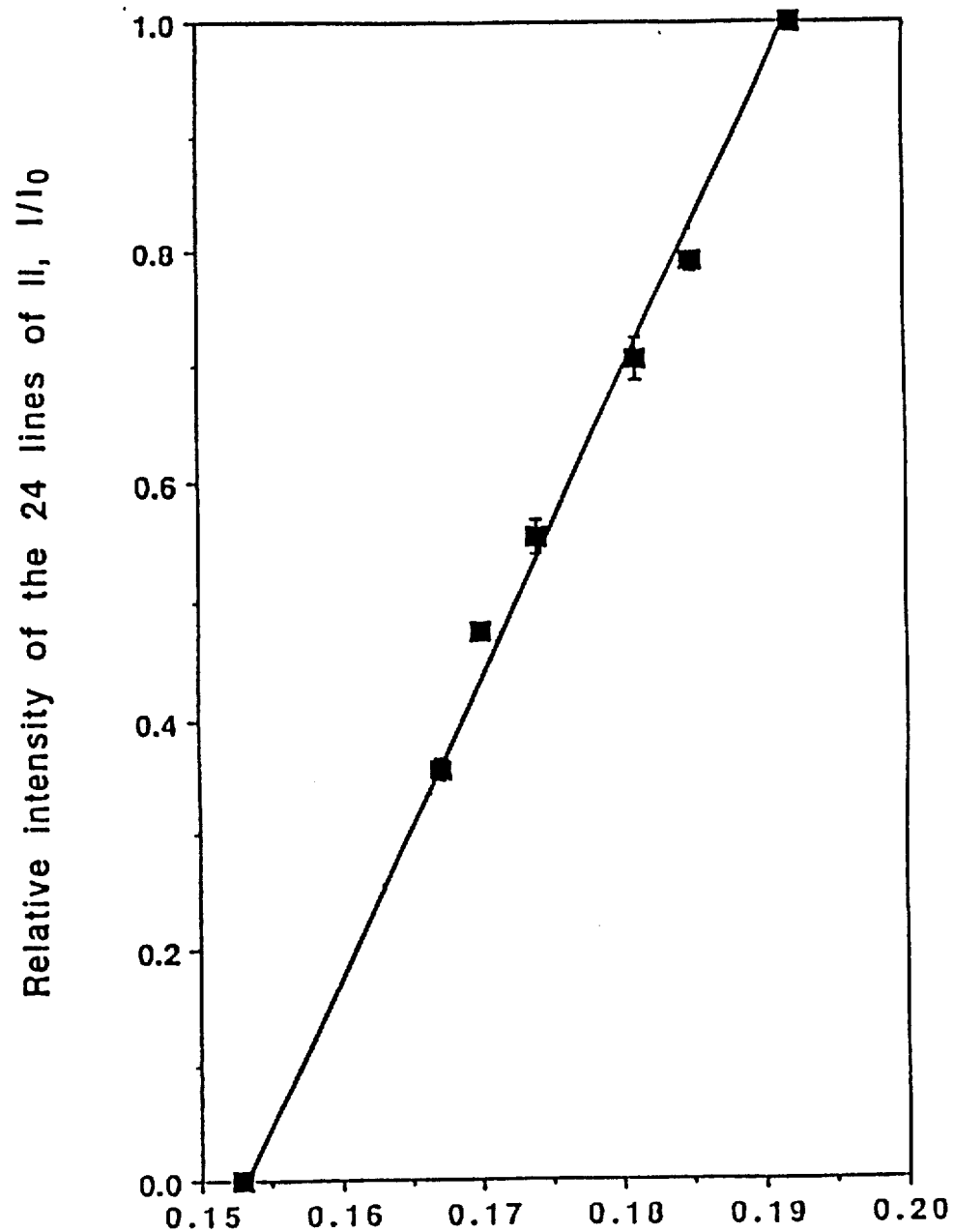

FIG. 9 is a plot of the relative intensities of the sum of 24 lines of carbamazepine as a function of:

$$\frac{1}{x_1(\mu_1^* - \mu_2^*) + \mu_2^*}$$

The line is based on theoretical values while the data points are experimental measurements.

DETAILED DESCRIPTION OF THE INVENTION

EQUIPMENT

X-ray diffractometer devices are commercially available and may be easily adapted for use by modifying the sample holders thereof to hold the tablet form of interest. A tablet sample may be retained in place in a conventional holder by means of a small amount of molding clay or the like in the bottom of a sample holder cup. A suitable x-ray diffractometer is a Siemens (Model D500) wide angle x-ray diffractometer. Preferably the equipment is provided with software which permits automatic subtraction of the background counts for each peak so that a correction of the measured photon intensity for background counts at each line does not need to be performed manually.

THEORY

The theory underlying the analytical technique which has now been found applicable to tablet samples is described in detail by the previously mentioned references of Alexander & Klug, incorporated herein by reference. In the simple case of a two component mixture, component is considered the unknown and component 2 is designated the matrix (or excipient). The integrated intensity of line i of component 1 in a powder mixture is given as:

$$I_{i1} = \frac{Kx_1}{\rho_1[x_1(\mu_1^* - \mu_2^*) + \mu_2^*]}$$

where K is a constant $x_1$ and $\eta_1$ are the weight fraction and density of 1 respectively and $\mu_1^*$ and $\mu_2^*$ are respectively the mass absorption coefficients of 1 and 2.

The line i of component 1 should be so chosen that in the 2 $\theta$ range where this peak occurs, the matrix should not exhibit any diffraction peaks. The intensity of peak i of a sample consisting of only 1, $(I_{i1})_0$, is given as:

$$(I_{i1})_0 = \frac{K}{\rho_1 \mu_1^*} \quad (2)$$

Division of (1) by (2) yields:

$$\frac{I_{i1}}{(I_{i1})_0} = \frac{x_1\mu_1^*}{x_1(\mu_1^* - \mu_2^*) + \mu_2^*} \quad (3)$$

$\mu_1^*$ and $U_2^*$ can be calculated from the chemical formulae of 1 and 2, respectively. It is then possible to calculate the intensity ratio, $I_{i1}/(I_{i1})_0$ as a function of $x_1$ This ratio can also be experimentally obtained. The intensity of the peak i of a sample consisting of only 1 is determined $[(I_{i1})_0]$. This is followed by the determination of the intensity of the same peak in mixtures containing different weight fractions of 1 and 2 This enables the experimental intensity ratio, $I_{i1}/(I_{i1})_0$, to be obtained as a function of $x_1$. If the experimental system satisfies the assumptions based on which the above equations were derived, a good agreement between the calculated and experimental intensity ratios can be expected.

Compression of the samples is likely to cause preferred orientation and it is not possible to prevent this. An aspect of this invention is the discovery that when compressed to a certain pressure, particles tend to orient in only one specific manner. Consequently, the variability in the area of a particular peak should be small in replicate samples.

Particle size can affect the diffracted intensity of x-rays in other ways. The diffracted intensity from substances crystallizing with a high degree of perfection decreases when the crystallites are larger than 10–15 $\mu$. This is known as primary extinction. In particles smaller than this size, errors due to primary extinction are negligible. Moreover, especially for organic materials, it is unlikely that the crystals in pharmaceutical tablets have a very high degree of perfection. Consequently, although it is preferred that the crystalline material in the tablet have a particle size below 15 $\mu$, the inventive method may be useful for analysis of some tablets where the crystalline material has a larger particle size. Primary extinction effects in excipient materials such as microcrystalline cellulose and starch which do not crystallize with a high degree of perfection need not be considered.

The inventive analytical technique requires that the active ingredient be crystalline. It is preferred that the excipient ingredient be noncrystalline or poorly crystalline since the powder x-ray diffraction pattern of crystalline excipients may interfere with the powder x-ray diffraction pattern of the active ingredient. However, if non-interfering lines are available, crystalline excipients may also be used. Moreover, in suitable cases multiple active ingredients may be analyzed, using non-interfering lines for each ingredient and determining each active ingredient in succession.

It is generally preferred that the crystalline ingredient to be analyzed constitute a substantial weight fraction of the tablet. Desirably the weight fraction will be at least about 0.25. For some mixtures the minimum weight fraction may be as high as 0.40 in order for the procedure to give accurate results. For any given mixture, the minimum level can be readily determined by the procedures outlined below in the examples.

It is also necessary that the reference tablet consisting only of the crystalline ingredient which is used to determine the value be compressed under the same experimental conditions as the unknown tablet.

EXAMPLES

The analytical technique of the invention was tested on several model systems. Tablets were prepared by mixing an active pharmaceutical ingredient with an excipient and compressing the mixture into tablets. The tablets contained no other ingredients. In these systems, the active ingredient will be the unknown component and the excipient will be the matrix. Lithium carbonate was chosen as a model inorganic compound. Mixtures containing various weight fractions of lithium carbonate and microcrystalline cellulose were prepared and subject to x-ray analysis. Carbamazepine was chosen as a model organic compound. Since a major fraction of pharmaceuticals are organic compounds, this system was studied in greater detail than the inorganic system. When mixtures containing various weight fractions of carbamazepine and microcrystalline cellulose were prepared, the presence of microcrystalline cellulose interfered with some lines of carbamazepine. This permitted us to check the validity of the method in presence of an interfering matrix substance. Mixtures containing various weight fractions of carbamazepine and starch were also prepared and subjected to x-ray analysis.

Materials.

Lithium carbonate (Analytical Reagent: assay ($Li_2CO_3$) 99.61%) was supplied by Mallinckrodt (Paris, KY). Anhydrous carbamazepine (assay ($C_{15}H_{12}N_2O$) > 99%) was obtained from Sigma Chemical Company (St. Louis, MO). It was ground in a ball mill (Spex Mixer/Mill, Spex Industries, Metuchen, NJ) for 5 min using a sample holder and ball made of agate. Microcrystalline cellulose (Avicel PH-105) and corn starch (Pure-Dent B810) were obtained from the FMC Corporation (Philadelphia, PA) and the Grain Processing Corporation (Muscatine, IA), respectively. Ceric oxide was a Standard Reference Material supplied by the National Institute of Standards and Technology (Gaithersburg, MD). All the compounds were stored under ambient conditions (about 25° C.) in tightly capped bottles.

Microscopic examination of lithium carbonate and carbamazepine revealed irregularly shaped crystals. The longest dimensions of particles of lithium carbonate and carbamazepine were measured microscopically. More than 97% of the particles of lithium carbonate were >10 μin size. The remaining particles were greater than 10 μ and less than 13 μ in size. Microscopic examination of carbamazepine revealed that a significant fraction of the particles were greater than 10 μ in size. After grinding for 5 min in a ball mill, all the examined particles were less than 10 μ in size. The ground carbamazepine was used for x-ray analysis. The microcrystalline cellulose and starch were reported to have an average particle size of 20 and 15 μ respectively.

Weight loss on drying.

The weight loss on drying of starch and microcrystalline cellulose were determined according to the procedure outlined in the United States Pharmacopeia, Revision XXI (1985). The starch was heated at 120° C. for 4 hours. Microcrystalline cellulose was heated at 105° C. to constant weight.

Thermal analysis.

The system consisted of a thermogravimetric analyzer (Du Pont 951) attached to a data analysis system (Thermal Analyst 2000, Du Pont). About 20 mg of the sample was weighed into an aluminum sample pan and heated under a stream of nitrogen. Lithium carbonate and carbamazepine were heated from 30° to 175° C. while the microcrystalline cellulose and starch were heated from 30° to 120° C.

Powder x-ray diffractometry.

The tablets were exposed to CuKα radiation (40 kV × 30 mA) in the step-scan mode with increments of 0.02° 2θ in a Siemens (model D500) wide angle x-ray diffractometer. The Bragg-Brentano focusing geometry was used, with a 1° incident aperture slit, 0.15° detector slit and a scintillation counter as the detector. Counts were accumulated for 1 sec at each step.

Preparation of Lithium Carbonate Tablets.

Mixtures containing different weight fractions of lithium carbonate and microcrystalline cellulose were prepared. Three hundred (300) mg of the sample was accurately weighed and compressed in a hydraulic press (Fred S. Carver, Menomonee Falls, WI) to a pressure of 187 MPa and held for 5 min. The tablets obtained were 11 mm in diameter and about 2.2 mm thick. A glass x-ray sample holder, with a central cavity 11.5 mm in diameter was fabricated. The cavity had a depth of approximately 2.5 mm. Two small pieces of molding clay were put at the bottom of the holder, the tablet was dropped into the cavity and, using a flat glass slide, the tablet was gently pressed down until the holder surface and the tablet surface were coplanar. The use of a glass holder was necessary because aluminum diffracts x-rays between 35° and 40°θ. The tablets were scanned from 20° to 42° 2θ. Eight lines of lithium carbonate were used for the quantitative purposes and Table I contains the Miller indices of these lines. The angular range over which integration was carried out to obtain the area under these lines is also given in Table I.

TABLE 1

| The lines of lithium carbonate and carbamazepine used in the quantitative analysis | | |
|---|---|---|
| d-spacing, Å | Miller indices | Integration angles, degrees 2θ |
| Lithium carbonate | | |
| 3.03 | 111 | 28.84–29.80 |
| 2.92 | −202 | 29.92–31.00 |
| 2.81 | 002 | 31.06–32.62 |
| 2.63 | −112 | 33.42–34.48 |
| 2.49 | 020 | 35.62–36.28 |
| 2.43 | −311 | 36.38–37.30 |
| 2.28 | 021 | 38.96–40.12$^a$ |
| 2.26 | 310 | |
| Carbamazepine | | |
| 6.94 | 200 | 12.36–13.28$^a$ |
| 6.77 | −101 | |
| 6.49 | 101 | 13.32–13.82 |
| 6.24 | 011 | 13.82–14.38 |
| 5.90 | 210 | 14.38–15.52 |
| 5.79 | −111 | |
| 5.60 | 111 | 15.52–16.12$^a$ |
| 5.58 | 020 | |
| 5.18 | 120 | 16.52–17.50$^x$ |
| 4.74 | −211 | 18.02–18.96$^x$ |
| 4.55 | 211 | 18.96–19.92$^{a,x}$ |
| 4.49 | 021 | |
| 4.35 | 220 | 19.92–21.06$^a$ |
| 4.30 | −121 | |
| 4.04 | −301 | 21.30–2.42$^x$ |
| 3.80 | −311 | 22.42–23.60$^x$ |
| 3.72 | 221 | 23.0–24.20$^x$ |
| 3.59 | 130 | 24.20–25.66$^a$ |
| 3.57 | 012, 320 | |
| 3.38 | −202 | 25.70–28.26$^d$ |
| 3.34 | 031 | |
| 3.28 | 230 | |
| 2.81 | 222 | 31.20–32.42$^a$ |

TABLE 1-continued

The lines of lithium carbonate and carbamazepine used in the quantitative analysis

| d-spacing, Å | Miller indices | Integration angles, degrees 2θ |
|---|---|---|
| 2.79 | 040, −421 | |

<sup>a</sup>because of overlap, these lines were integrated as one peak.
*These lines could not be used in the analyses of tablets containing carbamazepine and microcrystalline cellulose.

Once the powder diffraction pattern was obtained, the software in the instrument permitted automatic subtraction of the background. This eliminated the need for manual subtraction of the background counts for each peak. The manual background subtraction has previously been successfully used in quantitative x-ray analysis. However, such a correction would have been very tedious in this study for several reasons. First, the integrated intensity of numerous lines is of interest and, therefore, the background correction would have to be performed for each line. Second, the powder x-ray diffraction patterns of the samples revealed that it would be inappropriate to assume that the background counts do not undergo any change as a function of the scanning angle. Therefore, the background counts would have to be determined in the region immediately surrounding each line. This would not be possible in several instances since the lines are close to one another.

Preparation of Carbamazepine Tablets.

Two hundred (200) mg of the sample was accurately weighed and compressed in a hydraulic press to a pressure of 125 MPa and held for 1 min. The tablets were 11 mm in diameter and 2 mm thick. An aluminum sample holder with a circular central cavity 11.2 mm in diameter and 2.3 mm deep was fabricated The tablet was mounted into the holder as described before. The sample was scanned from 10° to 35° 2 θ. The powder x-ray diffraction pattern of carbamazepine is given in FIG. 3. In tablets of carbamazepine and microcrystalline cellulose, the presence of the latter interfered with some lines of carbamazepine. Therefore, only 15 lines of carbamazepine could be used for quantitative purposes. However, in tablets composed of carbamazepine and starch, 24 lines of carbamazepine could be used for quantitative analyses (Table I).

Long and Short Term Instrumental Drift.

The quantitative nature of the work required detection and correction of any short and long term instrumental drift. Several oxide powders are available from the National Institute of Standards and Technology which can be used for checking the intensity response of x-ray diffractometers. Ceric oxide was used to check for long-term instrumental drift. The powder was filled into an aluminum holder with a central cavity 15×15×1.5 mm. At regular intervals, the 111 line of ceric oxide was scanned at increments of 0.01° from 27.60 to 29.30. 2θ. The coefficient of variation (CV) of all such samples pooled together was 1.7%. Therefore, the long-term instrumental drift was assumed to be small enough to not require any correction There was no measurable short-term instrumental drift during the time of analysis of each sample.

Results.

The powder x-ray diffraction pattern of lithium carbonate (FIG. 1a was identical to that of lithium carbonate reported in the Joint Committee on Powder Diffraction Standards (JCPDS), International Center for Diffraction Data, Swarthmore, Pa. (1980), Pattern Nos. 22-1141 and 22-1141A. The powder x-ray diffraction pattern of carbamazepine (FIG. 3a) was identical to that of β-carbamazepine reported in the JCPDS, Pattern No. 33-1565. Though carbamazepine can exist in different polymorphic forms, earlier studies had confirmed that the sample used consisted only of the β-form and was not a mixture of polymorphs. Samples of lithium carbonate and carbamazepine when heated on the TGA showed no detectable weight loss, suggesting the absence of both physically and chemically bound water.

The weight loss on drying starch (mean ±SD; n=4) was 8.53 ±0.45%. The percent weight loss observed in the TGA was 9.05 ±0.22. In case of microcrystalline cellulose, the weight loss on drying was 3.33 ±0.31% while the TGA revealed a percent weight loss of 3.18 μ 0.19. The experimentally observed weight losses agreed with the water contents of starch and microcrystalline cellulose reported to be 8.9% and 3.0% w/w by the manufacturers.

For the purposes of quantitative x-ray studies, it was necessary to calculate the mass absorption coefficients of lithium carbonate, carbamazepine, microcrystalline cellulose and starch. The mass absorption coefficient of a substance is simply the weighted average of the mass absorption coefficients of its constituent elements The procedure applies irrespective of the state (solid, liquid or gas) of the substance. The water content of microcrystalline cellulose (close to 3% w/w) was small enough to be considered negligible in mass absorption coefficient calculations. Since the starch contained a higher percentage of water, the mass absorption coefficient calculation was based on the assumption that the sample contained 9% w/w water. The mass absorption coefficients of lithium carbonate, carbamazepine, microcrystalline cellulose and starch were calculated to be 8.36, 5.21, 6.16 and 6.53 cm$^2$/g (CuK$\alpha$ radiation), respectively.

Figure 1:
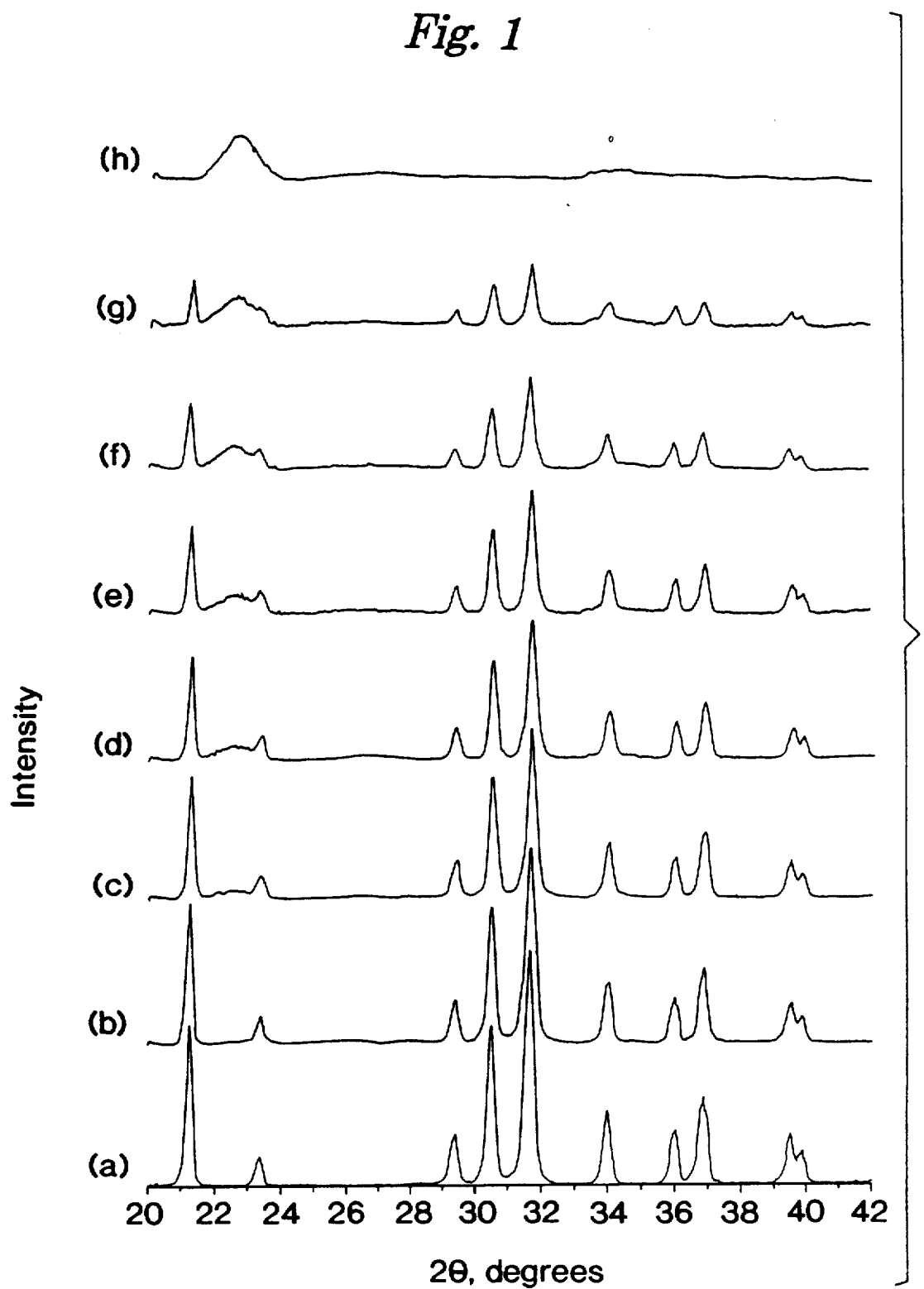
FIG. 1 is a stacked plot display of the background subtracted x-ray diffraction patterns of tablets of lithium carbonate (a), microcrystalline cellulose (h) and mixtures containing different weight fractions of lithium carbonate and microcrystalline cellulose. The weight fraction of lithium carbonate in the mixtures are: 0.85 (b), 0.75 (c), 0.60 (d), 0.50 (e), 0.40 (f) and 0.25 (g).
Figure 2:
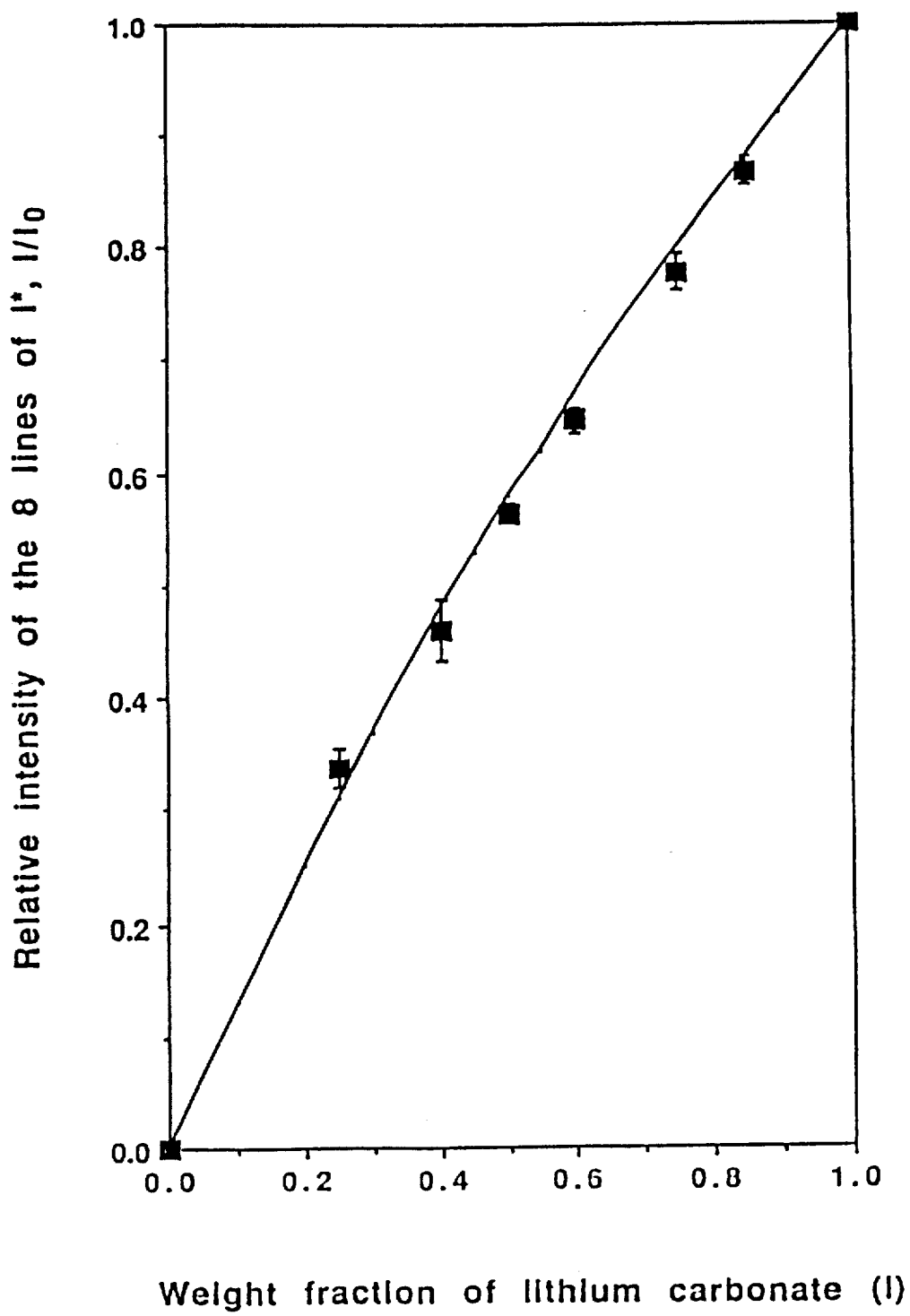
FIG. 2 is a plot of the relative intensities of the sum of 8 lines of lithium carbonate, identified in Table 1, as a function of the weight fraction of lithium carbonate in mixtures with microcrystalline cellulose. The line is based on theoretical values while the data points are experimental measurements. Error bars indicate standard deviation (n=3).

FIG. 1 is the stacked plot of the x-ray patterns of lithium carbonate, microcrystalline cellulose as well as mixtures containing different weight fractions of lithium carbonate and microcrystalline cellulose. In order to experimentally determine $(I_{11})_0$, the integrated intensities of the 8 lines of lithium carbonate were determined in a tablet made up of pure lithium carbonate and the intensity values were summed up. The sum of the integrated intensities of the same 8 lines of lithium carbonate were also determined in the mixtures containing various weight fractions of lithium carbonate and microcrystalline cellulose. This permitted the experimental determination of the intensity ratio as a function of the weight fraction of lithium carbonate in the tablet. As described earlier, these ratios were also calculated. In FIG. 2, the line is based on theoretical calculations while the data points are experimental measurements. There is a good agreement between the theoretical and experimental intensity measurements. The intensity ratio of a single line is expressed as $I_{11}/(I_{11})_0$ in Eq. (3) above. Since we are summing up the intensities of several lines, the intensity ratio will be expressed as $I/I_0$.

Figure 3:
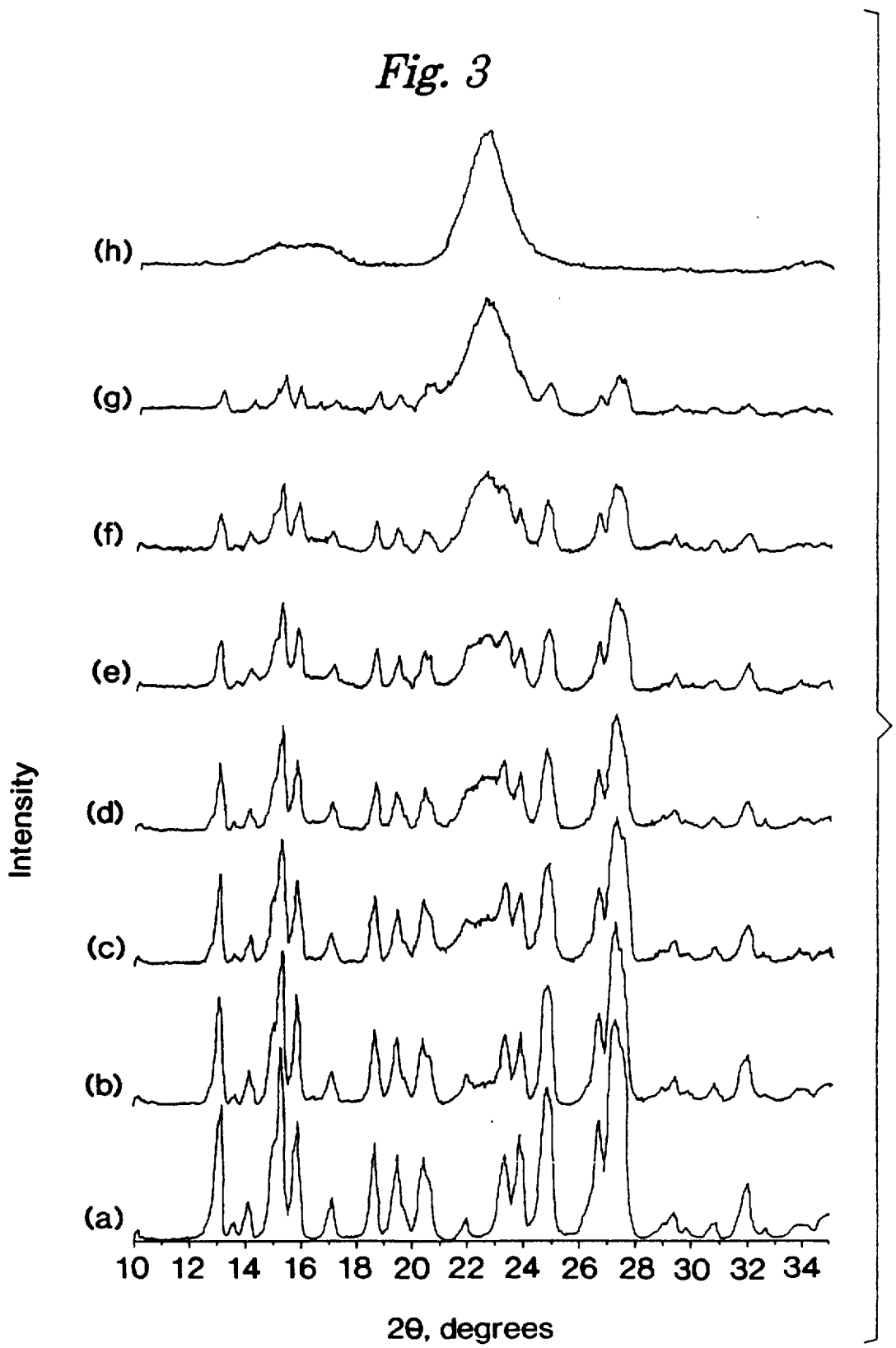
FIG. 3 is a stacked plot display of the background subtracted x-ray diffraction patterns of tablets of carbamazepine (a), microcrystalline cellulose (h) and mixtures containing different weight fractions of carbamazepine and microcrystalline cellulose. The weight fraction of carbamazepine in the mixtures are: 0.85 (b), 0.75 (c), 0.60 (d), 0.50 (e), 0.40 (f) and 0.25 (g).

FIG. 3 is the stacked plot of the powder x-ray diffraction patterns of carbamazepine, microcrystalline cellulose and mixtures containing different weight fractions of carbamazepine and microcrystalline cellulose. The figure reveals that in tablets containing carbamazepine and microcrystalline cellulose, the presence of the latter affects several lines of the former in the range of 16.5° to 24.2°. These lines could not be used in the quantitative analysis. Fifteen lines of carbamazepine were chosen for quantitative analysis and the integrated intensities of these lines were summed up. The d-spacings of these lines is given in Table I. In this case also, good agreement between the theoretical and experimental ratios were observed at all compositions (FIG. 4).

Figure 5:
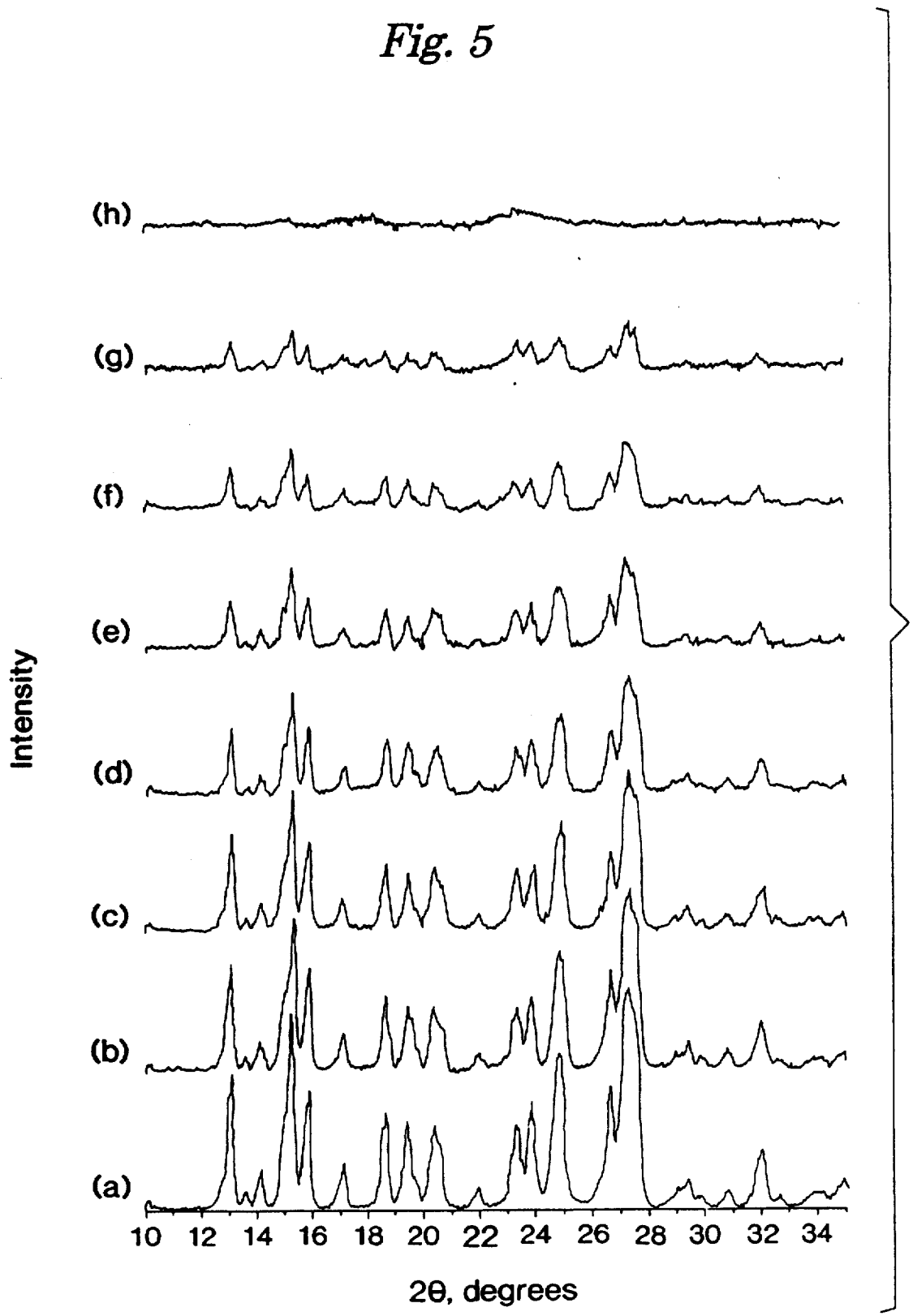
FIG. 5 is a stacked plot display of the background subtracted x-ray diffraction patterns of carbamazepine (a), starch (h) and mixtures containing different weight fractions of carbamazepine and starch. The weight fraction of carbamazepine in the mixtures are: 0.85 (b), 0.75 (c), 0.60 (d), 0.50 (e), 0.40 (f) and 0.25 (g).

FIG. 5 is the stacked plot of the powder x-ray diffraction patterns of carbamazepine, starch and mixtures containing different weight fractions of carbamazepine and starch. In this case, the presence of starch does not interfere with the x-ray pattern of carbamazepine. Therefore, 24 lines of carbamazepine listed in Table I could be used for the quantitative purposes. In this system, good agreement between the theoretical and experimentally observed intensity ratios were obtained only when the weight fraction of carbamazepine in the mixture was $\geq 0.4$ (FIG. 6).

Figure 4:
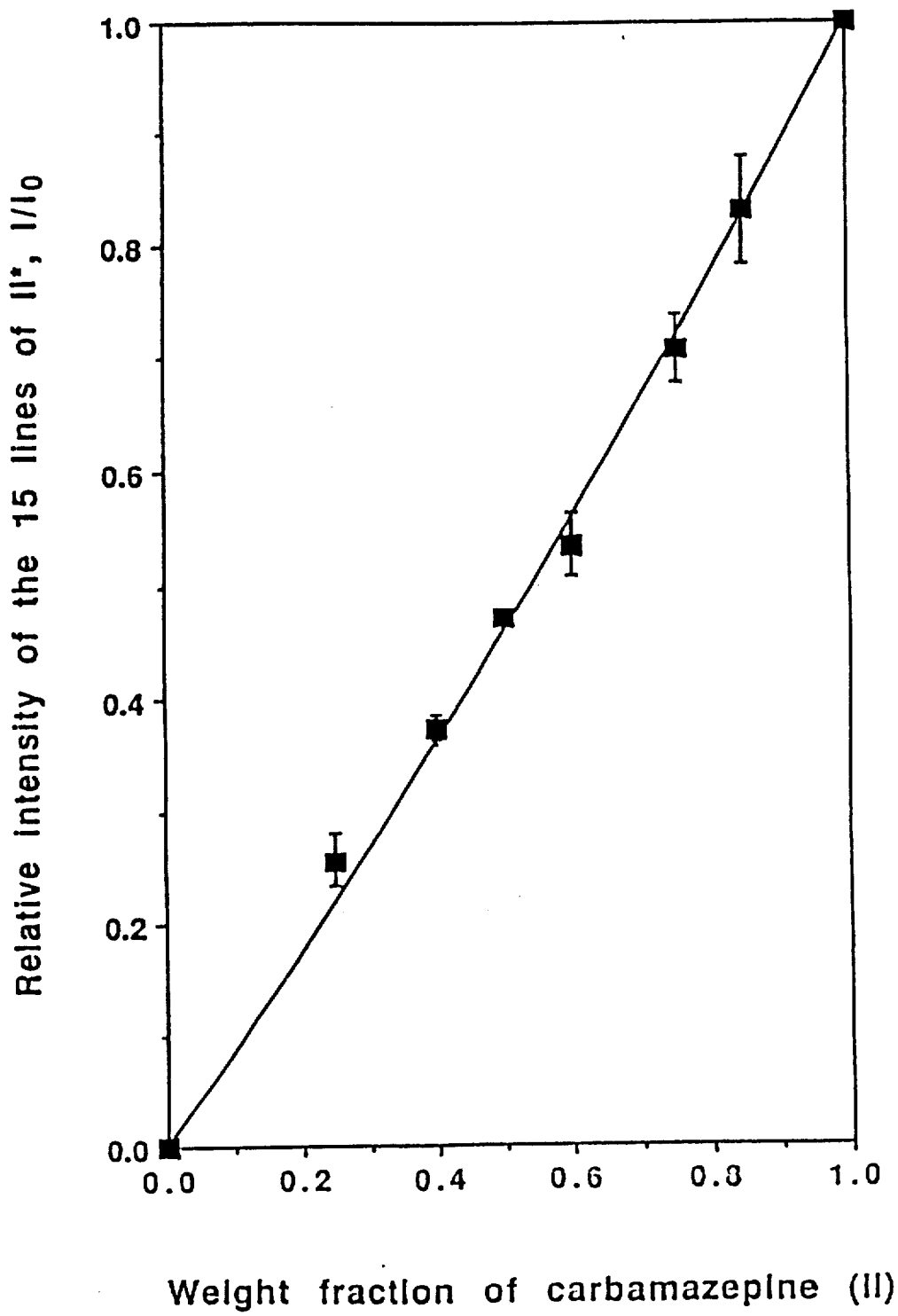
FIG. 4 is a plot of the relative intensities of the sum of 15 lines, identified in Table 1, of carbamazepine as a function of the weight fraction of carbamazepine in mixtures of carbamazepine and microcrystalline cellulose. The line is based on theoretical values while the data points are experimental measurements. Error bars indicate standard deviation (n=3).
Figure 6:
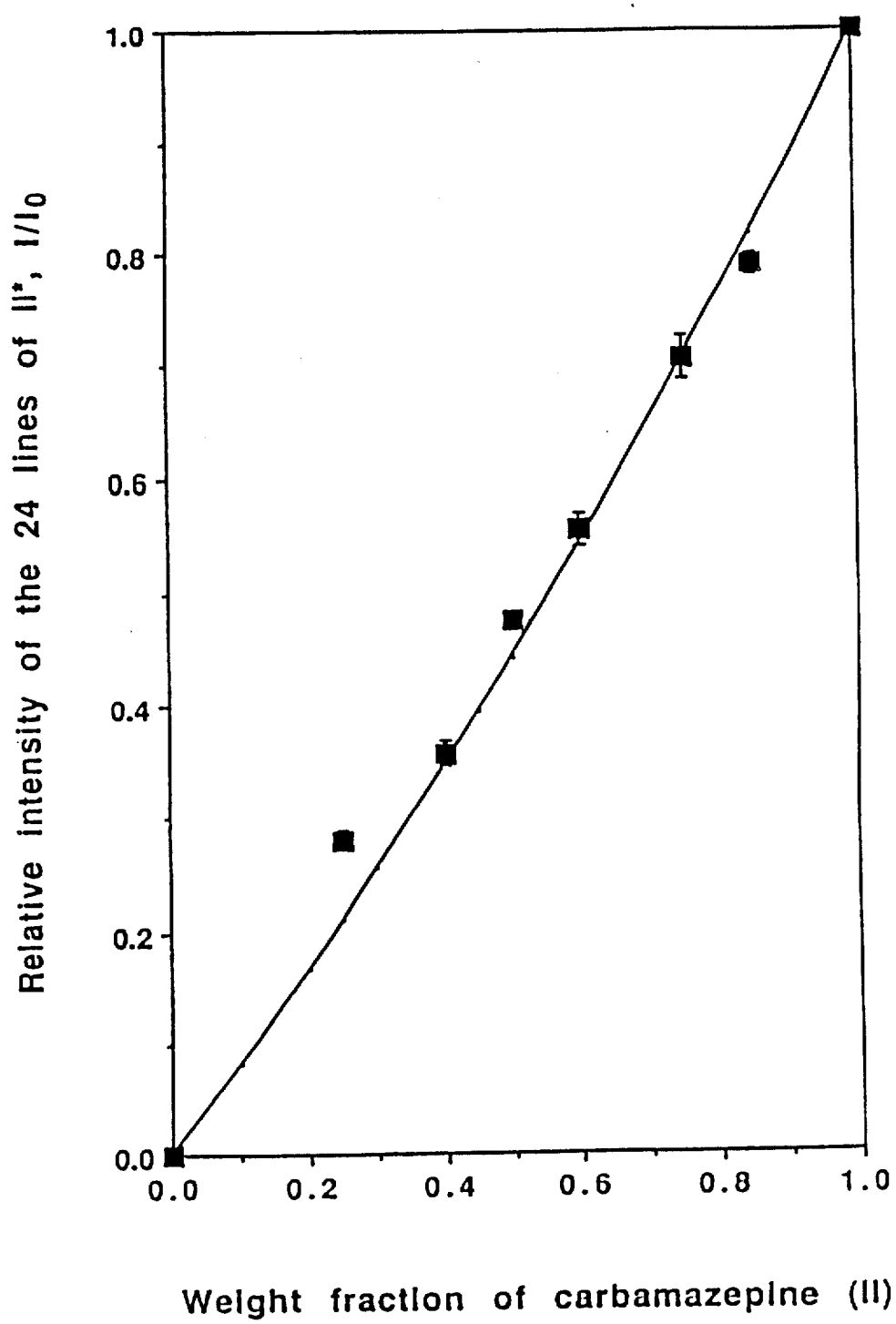
FIG. 6 is a plot of the relative intensities of the sum of 24 lines, identified in Table 1, of carbamazepine as a function of the weight fraction of carbamazepine in mixtures of carbamazepine and starch. The line is based on theoretical values while the data points are experimental measurements. Error bars (shown wherever larger than the symbols denoting the points) indicate standard deviation (n=3).

FIGS. 2, 4 and 6 are based on Eq. (3). This equation will yield a linear relationship between the intensity ratio $I_{11}/(I_{11})_0$, and the weight fraction of the unknown compound ($x_1$) only when the mass absorption coefficients of the unknown compound and the matrix are the same. This will be an uncommon occurrence. The modification of Eq. (3) yielded Eq. (4).

$$\frac{I_{i1}}{(I_{i1})_0} = \frac{\mu_1^*}{\mu_1^* - \mu_2^*} - \frac{(\mu_1^* \mu_2^*)}{\mu_1^* - \mu_2^*} \frac{1}{x_1(\mu_1^* - \mu_2^*) + \mu_2^*} \quad (4)$$

A plot of $I_{11}/(I_{11})_0$ as a function of:

$$\frac{1}{x_1(\mu_1^* - \mu_2^*) + \mu_2^*}$$

will result in a straight line. The slope and intercept on the y-axis of the line will be:

$$-\frac{\mu_1^* \mu_2^*}{\mu_1^* - \mu_2^*} \text{ and } \frac{\mu_1^*}{\mu_1^* - \mu_2^*}$$

respectively It is possible to calculate the intensity ratio, $I_{11}/(I_{11})_0$, as a function of:

$$\frac{1}{x_1(\mu_1^* - \mu_2^*) + \mu_2^*}$$

Figure 7:
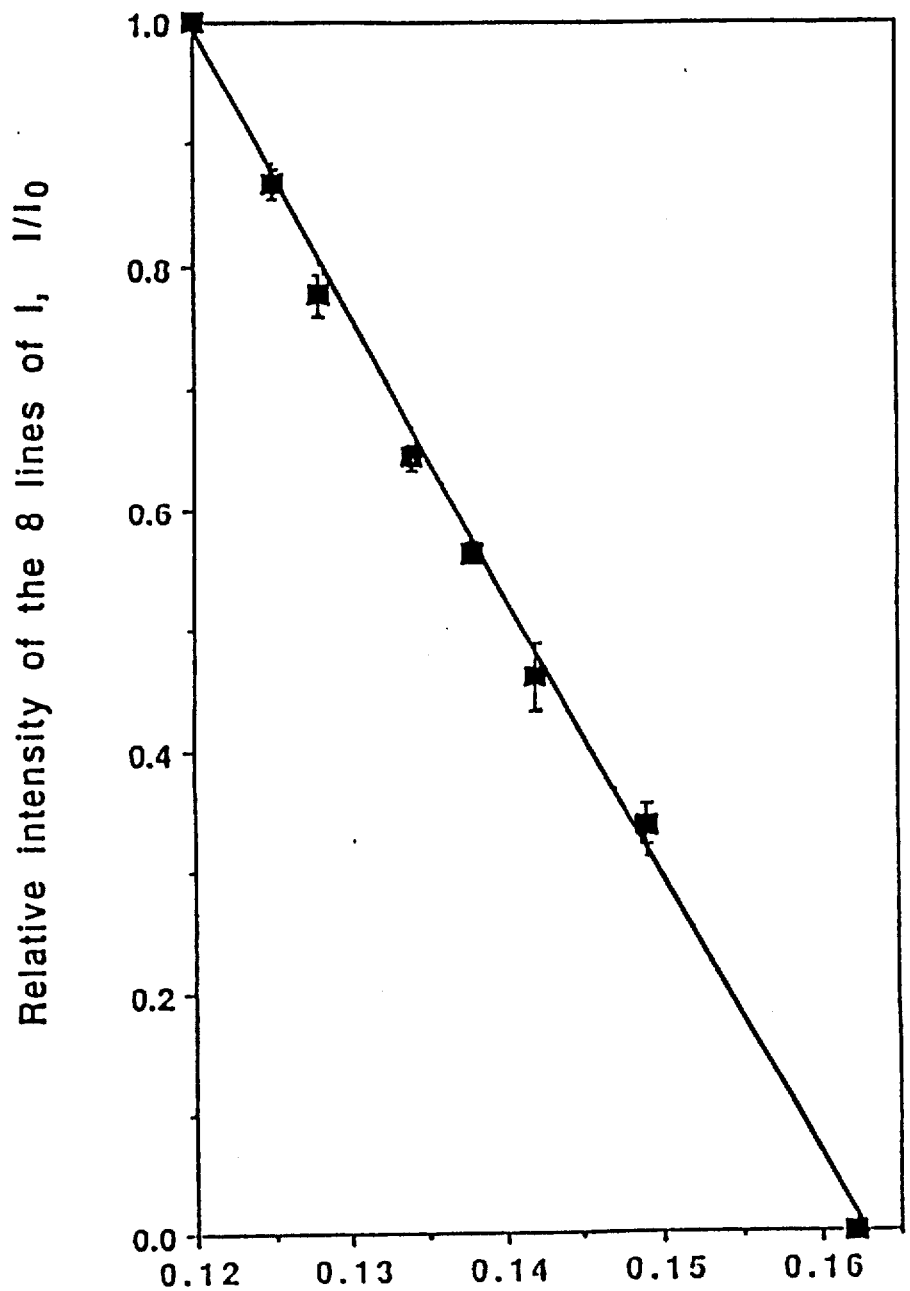

For the lithium carbonate-microcrystalline cellulose system, the line in FIG. 7 is based on the calculated intensity ratios while the data points are experimental measurements. The equation of the line was $y = 3.83 - 23.6x$. Such a line, obtained by substituting values of $\mu_1^*$, $\mu_2^*$ and $x_1$ into Eq. (4), will be hereafter referred to as calculated line. The equation of the straight line obtained by linear regression of the experimental data was $y = 3.61 - 22.1x$; $r^2 = 0.996$). Such a line, obtained on the basis of experimental data, will be hereafter referred to as experimental line.

From the experimentally observed intensity ratio, the weight fraction of lithium carbonate was calculated using both the calculated line and the experimental line (Table II). This then permitted the calculation of relative error for each determination. The relative error, expressed in percent, is given by the expression:

$$\frac{(\text{observed value} - \text{true value}) \times 100}{\text{true value}}$$

The results of these calculations indicate that when the weight fraction of lithium carbonate in the tablets is $\geq 0.25$, the relative error is always positive. However, much better distribution of the relative error is seen when the results are plotted based on the experimental line. This suggests that for determining the weight fraction of lithium carbonate in unknown tablets, the use of the experimental line is preferable. The highest value of the relative error was 11.8%. These results indicate that the x-ray method is suitable for quantifying the content of lithium carbonate in these tablets for weight fractions of lithium carbonate between 0.25 and 0.85.

TABLE II

Use of Eq. (4) to Determine the Weight Fraction of Lithium Carbonate in Tablets

| Weight Fraction of Lithium Carbonate In The Tablets | Weight Fraction of Lithium Carbonate (mean ± SD; n = 3) determined using: | |
|---|---|---|
| | calculated line[a] | experimental line[b] |
| 0.25 | 0.27 ± 0.00 | 0.27 ± 0.00 |
| 0.40 | 0.38 ± 0.03 | 0.39 ± 0.03 |
| 0.50 | 0.49 ± 0.01 | 0.49 ± 0.01 |
| 0.60 | 0.57 ± 0.01 | 0.58 ± 0.01 |
| 0.75 | 0.70 ± 0.02 | 0.73 ± 0.02 |
| 0.85 | 0.82 ± 0.02 | 0.86 ± 0.02 |

[a]The equation of the line is: $y = 3.83 - 23.6x$
[b]The equation of the line is: $y = 3.61 - 22.1x$ Similar studies were carried out on the carbamazepine-microcrystalline cellulose system. For the carbamazepine-microcrystalline cellulose system, the line in FIG. 8 is based on the calculated intensity ratios while the data points are experimental measurements. The equation of the calculated line was $y = -5.48 + 33.8x$. The equation of the straight line obtained by linear regression of the experimental data (experimental line) was $y = -5.36 + 33.1x$ ($r^2 = 0.997$). From the experimentally observed intensity ratio, the weight fraction of carbamazepine was calculated using both he calculated line and the experiment (Table III). The results show excellent agreement between the two determinations. When the weight fraction of carbamazepine in the tablets is between 0.40 and 0.85, the relative error was less than 10%. Therefore, the use of the x-ray method in these systems was reliable when the weight fraction of carbamazepine in the tablets is $\geq 0.4$. The relative error values determined using the calculated and the experimental are in close agreement. Therefore, in these systems the composition of the unknown tablet can be determined using the theoretical line. In other words, a standard curve based on known tablet compositions (i.e. experimental) does not appear to be necessary.

TABLE III

Use of Eq. (4) to Determine the Weight Fraction of Carbamazepine in Tablets Containing Carbamazepine and Microcrystalline Cellulose

| Weight Fraction of Carbamazepine In The Tablets | Weight Fraction of Carbamazepine (mean ± SD; n = 3) determined using: | |
|---|---|---|
| | calculated line[a] | experimental line[b] |
| 0.25 | 0.29 ± 0.03 | 0.28 ± 0.03 |
| 0.40 | 0.42 ± 0.01 | 0.41 ± 0.01 |
| 0.50 | 0.52 ± 0.01 | 0.51 ± 0.01 |
| 0.60 | 0.58 ± 0.03 | 0.58 ± 0.03 |
| 0.75 | 0.74 ± 0.03 | 0.74 ± 0.03 |
| 0.85 | 0.86 ± 0.04 | 0.86 ± 0.04 |

[a]The equation of the line is: $y = 5.48 - 33.8x$
[b]The equation of the line is: $y = 5.36 - 33.1x$ For the carbamazepine-starch system, the line in FIG. 9 is based on the calculated intensity ratios while the data points are experimental measurements. The equation of the calculated line was $y = -3.95 + 25.8x$. The equation of the straight line obtained by linear regression of the experimental data (experimental line) was y −3.85 +25.3x (r² 0.997). For the carbamazepine-starch system, the weight fraction of carbamazepine was calculated from the experimentally observed intensity ratio using both the calculated line and the experimental line (Table IV). The results show excellent agreement between the two determinations. When the weight fraction of carbamazepine in the tablets is ≧ 0.40, the relative error was less than 10%. The use of the x-ray method in these systems was reliable when the weight fraction of carbamazepine in the tablets is ≧ 0.4. The relative error values determined using the calculated line and the experimental line are in close agreement. Therefore, in these systems, as in the carbamazepine-microcrystalline system, the composition of the unknown tablet can be determined using the calculated line.

TABLE IV

Use of Eq. (4) to Determine the Weight Fraction of Carbamazepine in Tablets Containing Carbamazepine and Starch

| Weight Fraction of Carbamazepine | Weight Fraction of Carbamazepine (mean ± SD; n = 3) determined using: | |
|---|---|---|
| In The Tablets | calculated line[a] | experimental line[b] |
| 0.25 | 0.33 ± 0.01 | 0.32 ± 0.01 |
| 0.40 | 0.41 ± 0.01 | 0.40 ± 0.01 |
| 0.50 | 0.53 ± 0.01 | 0.53 ± 0.01 |
| 0.60 | 0.61 ± 0.01 | 0.61 ± 0.01 |
| 0.75 | 0.75 ± 0.02 | 0.75 ± 0.02 |
| 0.85 | 0.83 ± 0.01 | 0.83 ± 0.01 |

[a]The equation of the line is: y = 3.95 − 25.8x
[b]The equation of the line is: y = 3.85 − 25.3x The experimental intensity values were obtained by summing up the intensities of several lines. The integrated intensities of the individual lines was also highly reproducible. The coefficient of variation (CV) of the lines in some representative tablets of lithium carbonate and carbamazepine are given in Tables V and VI respectively. These results show that only rarely do the CV values of the integrated intensities go above 12% and in most instances the CV values are less than 10%.

TABLE V

CV of the Integrated Intensities of the Lines of Lithium Carbonate In Tablets Containing (a) Only Lithium Carbonate and (b) Different Proportions of Lithium Carbonate and Microcrystalline Cellulose

| d-spacing, Å | Weight Fraction of Lithium Carbonate | | | |
|---|---|---|---|---|
| | 1.00 | 0.85 | 0.60 | 0.25 |
| | Coefficient of variation, % | | | |
| 3.03 | 2.2 | 2.3 | 1.2 | 5.1 |
| 2.92 | 2.6 | 2.3 | 1.6 | 6.1 |
| 2.81 | 2.1 | 2.3 | 1.6 | 6.1 |
| 2.63 | 2.3 | 5.9 | 3.6 | 4.6 |
| 2.49 | 1.2 | 0.67 | 2.4 | 6.1 |
| 2.43 | 2.6 | 1.5 | 1.4 | 5.6 |
| 2.28 | 2.3 | 2.6 | 1.9 | 0.66 |
| 2.26 | | | | |

TABLE VI

CV of the Integrated Intensities of the Lines of Carbamazepine In Tablets Containing (a) Only Carbamazepine, (b) Different Proportions of Carbamazepine and Starch, and (c) Different Proportions of Carbamazepine and Microcrystalline Cellulose

| d-spacing, Å | Tablets containing only Carbamazepine | Tablets containing starch | | | Tablets containing microcrystalline cellulose | | |
|---|---|---|---|---|---|---|---|
| | | Weight fraction of Carbamazepine | | | | | |
| | | 0.85 | 0.60 | 0.25 | 0.85 | 0.60 | 0.25 |
| | Coefficient of variation, % | | | | | | |
| 6.94 | 2.8 | 3.6 | 6.7 | 5.5 | 0.9 | 4.3 | 1.6 |
| 6.77 | | | | | | | |
| 6.49 | 4.1 | 4.4 | 4.8 | 6.4 | 6.6 | 5.0 | 8.8 |
| 6.24 | 2.5 | 3.9 | 4.2 | 3.7 | 1.3 | 2.8 | 5.2 |
| 5.90 | 1.2 | 2.5 | 2.1 | 1.1 | 0.14 | 1.6 | 6.9 |
| 5.79 | | | | | | | |
| 5.60 | 2.3 | 3.9 | 1.6 | 5.1 | 1.9 | 3.4 | 7.7 |
| 5.58 | | | | | | | |
| 5.18 | 9.9 | 1.6 | 1.9 | 14 | 0.2 | 5.0 | 4.2 |
| 4.74 | 5.6 | 2.6 | 0.89 | 5.9 | 1.3 | 7.1 | 1.8 |
| 4.55 | 6.2 | 4.5 | 0.23 | 6.0 | 2.4 | 6.1 | 1.5 |
| 4.49 | | | | | | | |
| 4.35 | 7.8 | 6.9 | 1.9 | 4.1 | 4.6 | 4.3 | 2.4 |
| 4.30 | | | | | | | |
| 4.04 | 16 | 2.1 | 7.2 | 13 | — | — | — |
| 3.80 | 1.2 | 6.5 | 12 | 23 | — | — | — |
| 3.72 | 1.9 | 8.9 | 12 | 11 | — | — | — |
| 3.59 | 2.1 | 3.8 | 9.6 | 12 | 11 | 13 | 14 |
| 3.57 | | | | | | | |
| 3.38 | 1.6 | 2.6 | 2.3 | 4.7 | 7.3 | 4.6 | 14 |
| 3.34 | | | | | | | |
| 3.28 | | | | | | | |
| 2.81 | 2.7 | 3.9 | 8.8 | 4.8 | 6.7 | 8.7 | 1.0 |
| 2.79 | | | | | | | |

Compression of a solid may cause it to undergo a polymorphic transformation. However, the x-ray patterns of the compressed samples and the uncompressed powders were identical in case of both lithium carbonate and carbamazepine. Therefore, it was concluded that lithium carbonate and carbamazepine do not undergo polymorphic transformation when compressed to pressures of 187 and 125 MPa respectively. Similarly, lithium carbonate when compressed in presence of microcrystalline cellulose and carbamazepine when compressed in presence of microcrystalline cellulose or starch did not appear to undergo any polymorphic transformations (FIGS. 1, 3 and 5).

The data presented in Tables V and VI demonstrate that the variability in the area of a particular peak is small in replicate samples.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated. In particular, it should be noted that while the examples have been limited to mixtures of an active pharmaceutical ingredient and a single excipient ingredient, the method also works well where the excipient component comprises two or more non-crystalline or poorly crystalline ingredients.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method for quantitatively analyzing a known crystalline ingredient in a first compressed tablet consisting essentially of a solid mixture of the crystalline ingredient and an excipient component, the method comprising:

irradiating the tablet with x-rays in a powder x-ray diffraction device and determining an intensity value, I, indicative of the quantity of diffracted x-rays at an angular range producing at least one x-ray diffraction line characteristic of said crystalline ingredient;

determining the ratio of said value I to a diffracted x-ray intensity value, $I_0$, obtained on a second compressed tablet consisting of said crystalline ingredient at said angular range; and comparing the determined ratio $I/I_0$ to a set of predetermined standard values of said ratio for mixtures of said crystalline ingredient and said excipient component to quantitate said crystalline ingredient in said first compressed tablet.

2. A method as in claim 1 wherein said crystalline ingredient comprises at least 25% by weight of the solid mixture.

3. A method as in claim 1 wherein said predetermined standard values are calculated according to the relationship:

$$\frac{I}{(I)_0} = \frac{\mu_1^*}{\mu_1^* - \mu_2^*} - \frac{(\mu_1^* \mu_2^*)}{\mu_1^* - \mu_2^*} \frac{1}{x_1(\mu_1^* - \mu_2^*) + \mu_2^*}$$

where $\mu_1^*$ is the mass absorption coefficient for said crystalline ingredient, $\mu_2^*$ is the mass absorption coefficient for said excipient component and $x_1$ is the weight fraction of said crystalline ingredient in the mixture.

4. A method as in claim 1 wherein said set of predetermined standard values is determined experimentally from a plurality of compressed tablet samples of known mixtures of said crystalline ingredient and said excipient component.

5. A method as in claim 1 wherein the said first tablet is a pharmaceutical tablet and said crystalline ingredient comprises the active ingredient thereof.

6. A method as in claim 1 wherein said crystalline ingredient comprises at least 40% by weight of said solid mixture.

7. A method as in claim 1 wherein said crystalline ingredient comprises no more than 85% by weight of said solid mixture 8. A method as in claim 5 wherein the excipient component is selected from microcrystalline cellulose and starch.

9. A method as in claim 1 wherein the excipient component is a non-crystalline or poorly crystalline material.

10. A method as in claim 1 wherein the excipient comprises a plurality of non-crystalline or poorly crystalline ingredients.

* * * * *

UNITED STATES PATENT AND TRADEMARK OFFICE
CERTIFICATE OF CORRECTION

PATENT NO. : 4,991,191

DATED : February 5, 1991

INVENTOR(S) : Suryanarayana, Raj G.

It is certified that error appears in the above-identified patent and that said Letters Patent is hereby corrected as shown below:

On the front title page of the patent, in the title itself, delete "table" and insert -- tablet delete "power" and insert -- powder --

Col. 1, line 3, delete "table" and insert -- tablet

Col. 1, line 3, delete "power" and insert -- powder --

Signed and Sealed this

Fourth Day of August, 1992

Attest:

DOUGLAS B. COMER

Attesting Officer

Acting Commissioner of Patents and Trademarks